(12) United States Patent
Pan et al.

(10) Patent No.: US 7,700,326 B2
(45) Date of Patent: Apr. 20, 2010

(54) RT-PCR DETECTION FOR DIFFERENTIAL DIAGNOSIS OF FIELD ISOLATES OR LAPINIZED VACCINE STRAIN OF CLASSICAL SWINE FEVER VIRUS (CSFV) IN SAMPLES

(75) Inventors: Chu-Hsiang Pan, Taipei County (TW); Ming-Hwa Jong, Taipei County (TW)

(73) Assignee: Animal Health Research Institute, Council of Agriculture, Executive Yuan, Taipei County (TW)

( * ) Notice: Subject to any disclaimer, the term of this patent is extended or adjusted under 35 U.S.C. 154(b) by 589 days.

(21) Appl. No.: 11/454,524

(22) Filed: Jun. 16, 2006

(65) Prior Publication Data
US 2006/0286551 A1 Dec. 21, 2006

(30) Foreign Application Priority Data
Jun. 17, 2005 (TW) .............................. 94120270 A

(51) Int. Cl.
*C12P 19/34* (2006.01)
(52) U.S. Cl. .................................................. 435/91.2
(58) Field of Classification Search ................. 435/91.2
See application file for complete search history.

(56) References Cited

U.S. PATENT DOCUMENTS

2006/0177818 A1* 8/2006 Hoffmann et al. ............... 435/5
2007/0072191 A1* 3/2007 Bartosch et al. ................. 435/6

OTHER PUBLICATIONS

McGoldrick et al. Journal of Virological Methods, vol. 79, pp. 85-95, 1999.*
Chu-Hsiang Pan et al., Rapid detection and differentiation of wild-type and three attenuated lapinized vaccine strains of Classical swine fever virus by reverse transcription polymerase chain reaction, J Vet Diagn Invest, 2008, pp. 448-456, vol. 20.

* cited by examiner

*Primary Examiner*—Gary Benzion
*Assistant Examiner*—Cynthia B Wilder
(74) *Attorney, Agent, or Firm*—WPAT, P.C.; Anthony King

(57) ABSTRACT

The present invention provides a rapid RT-PCR detection method and a diagnostic kit for differentiating field isolates of classical swine fever virus (CSFV) from lapinized CSF vaccine viruses in samples. In order to detecting different genotypes of CSF virus, this invention uses a pair (or pairs) of CSF virus specific primers designed from the conserved sequences within the 3'-untranslated region of CSFV which contains an insertion of 12~13 nucleotides (poly T) in the region of the lapinized CSF vaccine virus, in comparison with the corresponding region of field isolates of CSFV. By the RT-PCR or the RT-PCR followed by a nest-PCR, field isolates of CSFV and lapinized CSF vaccine viruses in samples could be detected directly and quickly and/or differentiated in electrophoresis without further enzymatic digestion or DNA sequencing.

5 Claims, 5 Drawing Sheets

SEQ ID NO: 1

The sequence of LPC vaccine virus between primers CP5 and CP6 (length 380 bp)

```
GTAGCAAGACTGGAAATAGGTACATGCCCGGAGAAGGCCA
CACCCTGCAAGGAAGACATTATGAAGAATTGGTGTTGGCA
AGGAAACAGATCAACAACTTTCAAGGACAGACAGGTACA
ATCTAGGCCCAATAGTCAACATGGTGTTGAGGAGGCTGAG
AGTCTTGATGATGACCTTGATAGGGAGAGGGTATGAGCG
CGGGTAATCTGGATCTGAACCCGCCAGTAGGACCCTATT
GTAGATAACACTAATTTTCTTTTTTTCTTTTTTATTTATT
TAGATTTATTATTTATTTATTTATTTATTGAATGA
GTAAGAATTGGTACAAACTACCTCAAGTTACCACACTACA
CTCATTTTTTAACAGCACTTT
```

Fig. 4

SEQ ID NO: 2

The sequence of Alfort187 strain of CSFV, between primers CP5 and CP6 (length 367 bp), sequence position on the Alfort187 (Accession No : X87939) is from 11,874 to 12,240

GTAGCAAGACTGGAAACAGGTACATACCTGGAGAGGGCCA
CACCCTGCAAGGGAGACATTATGAAGAACTGGTGTTGGCA
AGAAACAGATCAATAACTTTCAAGGGACAGACAGGTACA
ATCTAGGCCCAATAGTCAACATGGTGTTAAGGAGGCTGAG
AGTCATGATGATGACCCTGATAGGGAGAGGGGTATGAACG
CGGGCAACCCGGGATCTGGACCCGCCAGTAGGACCCTATT
GTAGATAACACTAATTTT-------------TTATTTATT
TAGATATTATTATTTATTTATTTATTTATTGAATGA
GTAAGAACTGGTACAAACTACCTCAAGTTACCACACTACA
CTCATTTTTTAACAGCACTTT

Fig. 5

RT-PCR DETECTION FOR DIFFERENTIAL DIAGNOSIS OF FIELD ISOLATES OR LAPINIZED VACCINE STRAIN OF CLASSICAL SWINE FEVER VIRUS (CSFV) IN SAMPLES

FIELD OF THE INVENTION

This invention relates to a method and a diagnostic kit for detection of the classical swine fever virus (CSFV), in particular the differentiation field isolates and lapinized vaccine strains of CSFV thereof, by reverse transcription-polymerase chain reaction (RT-PCR), alone or in combination with nest-PCR (n-PCR), in which at least a pair of CSFV-specific primers, each of which was designed based on the conserved sequences within the 3'-untranslated region of CSFV's genome, are used.

BACKGROUND OF THE INVENTION

Classical swine fever (CSF), previously referred to hog cholera (HC), is an important infectious disease of swine caused by CSFV. Domestic pigs and wild boar are susceptible to CSFV. The virus belongs to the genus *Pestivirus* within the family Flaviviridae, which also includes bovine viral diarrhea virus (BVDV) and border disease virus (BDV) (Matthaeus, *Zbl. Vet. Med.* 328: 126-132, 1981). They are antigenically and structurally closely related but CSFV can be distinguished from BVDV and BDV in serological and nucleotide differences (Paton, *J Comp pathol* 112: 215-236, 1995). The most commonly used in laboratory CSF diagnostic methods, such as immuno-fluorescence stain, enzyme linked immunosorbent assay (ELISA) and RT-PCR, can hardly distinguish the field isolates of CSFV from the lapinized CSF vaccine viruses. Records of CSF in Taiwan date back to 1938 (Lee, *Scientific Agri* (Taiwan), 2(11): 4-14). In an effort to control this highly contagious disease, a live attenuated vaccines made from a lapinized CSF vaccine virus, LPC strain, have been widely used in the field since 1958 in Taiwan (Lin, *National Science Council Special Publication* Number 5, 1-42, 1981). Vaccination significantly decreased the incidence. However, sporadic outbreaks were still reported occasionally. According to the current legislation on CSF in Taiwan, each piglet has to be vaccinated twice with the LPC vaccine virus in 3, 6 or 6, 9 weeks old, it depend on the decrease level of maternal antibody. Unfortunately, the vaccine virus can be detected and can't be differentiated from field isolates of CSFV by ELISA and RT-PCR in samples of pigs. Since the LPC vaccine virus interfered with the laboratory diagnosis of CSF, the RT-PCR amplicons always proceed with nucleotide sequencing to exclude the interference by LPC vaccine virus in Taiwan.

A tentative assignment of world isolates of CSFV by genotyping has been divided it into three groups with three or four subgroups: 1.1, 1.2, 1.3; 2.1, 2.2, 2.3; 3.1, 3.2, 3.3, 3.4 (Paton, *Vet. Microbiol.* 73: 137-157, 2000). Phylogenetic analysis of the E$^{rns}$ and E2 sequences of 158 CSFVs, which were isolated in the field in Taiwan between 1989 and 2003, shows that four distinct CSFVs genotypes existed in Taiwan including one endemic strain (subgroup 3.4) and three introduced strains (subgroup 2.1a, 2.1b and 2.2). The analysis also shows the LPC strain doesn't belong to the aforementioned four subgroups, but to the subgroup 1.1. (Pan, *Arch Virol*, 150(6): 1101-19, 2005).

There are four lapinized CSF vaccine viruses, namely LPC, HCLV, Chinese C and Riem C, widely utilized in the world nowadays. The LPC strain was derived from the Rova strain of CSFV, which had already undergone about 250 serial passages in rabbits by Lederle Laboratory in Philippines and was introduced into Taiwan by Dr. Chung-Tao LEE in 1952 (Lee, Scientific Agri (Taiwan), 2(11): 4-14). The pigs inoculated with this virus showed a severe post-vaccinated reaction and a few of them even died of CSF after vaccination. In order to obtain a highly safe and potent strain for CSF vaccination, the virus was then rapidly and carefully serial-passaged through native Taiwan rabbits. After more than 800 passages in rabbits, it proved extremely safe for pigs and highly effective against CSFV (Lin, National Science Council Special Publication Number 5, 1-42, 1981). Nowadays, the LPC vaccine is widely utilized to protect pigs from CSF in Taiwan. The HCLV strain was derived from the wildtype strain Shimen by 480 passages in the bodies of rabbits in China in 1950s. (Wu, Virus Genes, 23(1): 69-76, 2001). The Chinese C strain is a cell culture adapted derivative of HCLV strain. (Oleksiewicz, Veterinary microbiology, 92:311-325, 2003). The Riem C strain is a cell culture adapted derivative of HCLV strain and used as bait vaccine in Europe (Oleksiewicz, Veterinary microbiology; 92:311-325, 2003). Wu et al. (Virus Genes, 23(1): 69-76, 2001) have sequenced HCLV strain and discovered one notable insertion of 12 continuous nucleotides, CTTTTTTCTTTT (SEQ ID NO:8) in the 3'-untranslated region of HCLV genomic cDNA when compared with its parental virulent Shimen strain. Wong et al (Virus Genes; 23(2): 187-92, 2001) also sequenced the whole genome of LPC vaccine strain and found that an insertion 0113 nucleotides, TTT(C/T)CTTTTTTTT SEQ ID NO:9, in the 3-untranslated region of LPC vaccine strain. The inventors of the present invention had also compared all the CSFV sequences from the GenBank and found that only the four lapinized CSF vaccine viruses, LPC, HCLV, Chinese C and Riem C strains, have an insertion of 12~13 nucleotides in their 3-untranslated regions and the insertion is not found in the field isolates of CSFV. Other non-lapinized CSF vaccine viruses, such as Japanese GPE- and Russian CS vaccine strains, also do not have the insertion.

Vaccination is one of the most successful tools for the prevention of CSFV infection. Unfortunately, the use of laboratory diagnostic methods to detect CSFV could be interfered by vaccine virus when attenuated vaccines are in use. For this reason it is of interest to know how long after vaccination can the vaccine strain be detected in samples that are commonly used for diagnostic procedures. To study the duration of vaccine virus distribution in piglets, Lorena et al. (*Veterinary microbiology*, 81: 1-8, 2001) inoculated piglets with the Chinese C strain vaccine virus and studied the distribution of vaccine virus in organ samples of inoculated piglets. He found that the virus can be detected in tonsil on post-inoculation day (PID) 6, 8, 10, 13 and 16 using ELISA and in blood samples on PID 2, 4, 6, 8, 10, 13, and 16 using RT-PCR. Therefore, he emphasized that this factor must be considered in routine diagnostic procedure, when vaccination against CSF with a live vaccine is carried out. In Germany, CSF was present in wild boar in different federal states (*Veterinary microbiology*, 82: 301-310, 2001). Infection in domestic pigs was usually caused by direct or indirect contacts with infected wild boars. Wild boars distributed in the woods and they are difficult to be caught for injecting CSF vaccine. Therefore, Oral application of CSF vaccines (lapinised or cell culture vaccines) is necessary and has been investigated in Europe (*Veterinary microbiology*, 73: 239-252, 2000). Kaden et al. (*J Vet Med B Infect Dis Vet Public Health*, 51(6): 260-2, 2004) studied the persistence period of the Chinese C strain vaccine virus in immunized animals after oral vaccination. The results show that the C strain virus can be found in organs until day 8 post-vaccination (pv) in domestic pigs and until day 9 pv in wild boars. In the CSF endemic countries like Taiwan where vaccination program with live vaccine is carried out, the vaccine virus can probably be detected in the blood and lymphatic tissue samples such as tonsil, lymph nodes and spleen. Therefore, diagnosis with the commonly used diagnostic methods such as immuno-fluorescence stain, ELISA and RT-PCR can be interfered by the vaccine virus.

Virus isolation, ELISA and RT-PCR are the most commonly used methods for CSF laboratory diagnosis. Paton et al. (*Veterinary microbiology* 73: 159-174, 2000) show that the order of the sensitivity was RT-nested PCR>RT-PCR>virus isolation>ELISA when applying these methods to clinical samples in CSF diagnosis. Dewulf et al. (*Journal of Virological Methods* 119: 137-143, 2004) compare several CSF laboratory diagnostic techniques on live animals for detection of infection. He concluded that the RT-nPCR technique is the best diagnostic tool available for early detection of a CSF infection. A real-time RT-PCR for the simple and rapid diagnosis of CSF has been developed and evaluated in experimentally infected swine and clinical samples (Risatti, *Journal of Clinical Microbiology;* 41(1): 500-505, 2003; Risatti, *Journal of Clinical Microbiology,* 43(1): 468-471, 2005). Accordingly, real-time RT-PCR is recognized as a sensitive method for rapid diagnosis of CSF. However, no real-time RT-PCR for distinguishing the field isolates of CSFV from the lapinized CSF vaccine viruses has been established.

The RT-PCR and nucleotide sequencing are widely used as the methods to solve this problem. The disadvantage of these methods includes the laborious process of the methods and the incapability of screening large field samples. Zaberezhny et al. (*Dtsch Tierarztl Wochenschr.* September; 106(9): 394-7, 1999) have used RT-PCR and restriction enzyme digestion for differentiation between Russian vaccine strain from field isolates of CSFV. Vilcek et al. (*Acta Vet Scand.* 39(3): 395-400, 1998) also used restriction endonuclease cleavage of PCR amplicons to distinguish the vaccine strain from European field strains. These are the two documents available about the utilization of the RT-PCR and restriction enzyme digestion method to differentiate the vaccine virus and field isolates of CSFV; besides, the prior art can only distinguish the two viruses by RT-PCR followed by nucleotide sequencing. Thus there is no prior disclosed information concerning the utilization of the characteristic of one 12~13 nucleotides inserting in the genome of the 3'-untranslated region of the lapinized CSF vaccine viruses to establish a differential RT-PCR without combination with other technique. CSFV specific primers are designed to amplify the aforementioned 3'-untranslated region and then the size of the RT-PCR amplicons can be compared directly by electrophoresis without further processing the complicated enzymatic digestion and nucleotide sequencing to determine the existence of the field isolates of CSFV and lapinized CSF vaccine viruses and to differentiate between them. The diagnosis of CSF can thus be more rapid, convenient and the interference from the vaccine virus can be more correctly excluded.

SUMMARY OF THE INVENTION

For solving the problem of the interference from the lapinized CSF vaccine viruses with the laboratory diagnosis of CSF. This invention relates to a method and a diagnostic kit for detection of CSFV and differentiation of field isolates and lapinized vaccine strains, by RT-PCR, alone or in combination with nest-PCR. By a pair (or pairs) of CSFV specific primers designed from the conserved region of the 3'-untranslated region of CSFV which there are an insertion of 12~13 nucleotides in the 3'-untranslated region of the lapinized CSF vaccine viruses, in comparison with the corresponding region of field isolates of CSFV, to perform the nucleotide expansion methods, such as RT-PCR or n-PCR, and to separate the PCR products by electrophoresis (the better embodiment is by using the 3-4% agarose gels) for direct analysis of the results. The size of the RT-PCR amplicons can be compared directly by electrophoresis without further processing the complicated enzymatic digestion and nucleotide sequencing to determine the existence of the field isolates and lapinized CSF vaccine virus and to differentiate between them. Therefore, the field isolates of CSFV can be rapidly differentiating from lapinized CSF vaccine viruses.

The term "field isolates of CSFV" used in the present invention refers generally to the CSFV isolated from the pigs in the field and not serial-passaged in rabbits or other animals.

The term "lapinized classical swine fever vaccine viruses" used in the present invention refers to the CSFV strain obtained from high passages in rabbits for further utilization as CSF vaccine. Four attenuated lapinized CSF vaccine viruses nowadays widely utilized in the world as a vaccine: the LPC strain, the HCLV strain, the Chinese C strain and the Riem strain.

The term "nucleic acid" used in the present invention refers to DNA (deoxyribonucleic acid) or RNA (ribonucleic acid) and their single or double stranded polymers (poly nucleotides). Unless limited, the term includes those nucleic acids having similar binding characteristics with the reference nucleic acid and those natural nucleic acid analogues already known and metabolize in a similar way as natural nucleic acids.

The term "same" or "unique" in percentage about two or more nucleotide or protein sequences refers to two or more sequences or sub-sequences which have the same or the same percentage of the amino acid residues or nucleotides, while using one of the sequence-comparison algorithms (e.g. Smith-Waterman algorithm) or processing the maximum-corresponding comparison and ranking by visual measure mentioned in this text.

Concerning the sequence-comparison, a section of sequence is taken as a reference for the testing sequence to compare. When applying sequence-comparison algorithm, the testing sequence is entered into the computer as well as the reference one, the sub-sequence coordinate can be assigned if necessary, and the parameters of the sequence algorithm program should be set. The sequence-comparison algorithm can then, based on the program parameters set, calculate the percentage of uniqueness of the testing sequence compared to the reference sequence.

The term "amplification of DNA or RNA sequence" used in the present invention refers to all methods that allow the amplification of the number of the sample of the targeted nucleotide sequence. The most widely used nucleotide sequence expansion technology is PCR. Basically, it means attaching two primers, which are respectively sense primer and antisense primer to the denaturalized DNA stroma and extending by using thermo-stable DNA polymerase. The later can catalyze RT-PCR (reverse-transcript PCR) and real-time PCR in rapid and repeating cycles. (In a three-step PCR, it means denaturalization/annealing/extension; in a two-step PCR, it means denaturalization/annealing and extension.). RT-PCR can be performed with a single thermo-stable enzyme with reverse-transcription enzymes and DNA polymerase (Maire and Jefferan, 1999). Optionally, it can also be performed with a single test-tube reaction (Kathy et al., biological technology 17:1034-1036, 1994) containing both enzymes (reverse-transcription enzyme and thermo-stable DNA polymerase).

The term "nest polymerase chain reaction (nest-PCR or n-PCR)" refers to the improved design which can increase the sensitive of PCR, i.e. the secondary PCR which concerns the design of a pair of primers on the PCR product to perform the secondary PCR, the sensitivity can thus increase by 100 to 1000 times.

The term "3'-untranslated region of CSFV nucleic acid" is defined as the 3'-untranslated region of nucleotide-sequence of the LPC vaccine virus (SEQ ID NO: 1) which corresponds to the nucleotide section (SEQ ID NO: 2) from 11,874 to 12,240 base pairs (bp) of 3' nucleotide positioned on Alfort 187 strain (Accession No: X87939) of the CSFV and includes other isogenic classical swine fever vaccine strains attenuated by rabbits such as the 3' nucleotide sequence of LPC, HCLV, Chinese C and Riem strain. According to the present invention, the 3'-untranslated region of the nucleotide of lapinized CSF vaccine strains comprises an insertion of 12~13 nucleotides in comparison with the field isolates of CSFV (equivalent to the poly T segment "CTTTTTTTCTTTT" as shown in SEQ ID NO: 1).

The term "comprising equivalent nucleotide as assigned SEQ ID NO" refers that the nucleotide region defined by the SEQ ID NO (or any equivalence or any related part) is included in the interested nucleotide molecule. The term "equivalence" in the present invention includes variants (such as polymorphic variants) and derivatives (such as modified variants).

The term "primer" refers to a short nucleic acid structure, which can be the starting point of the replication of nucleic acid. While carrying out the PCR reaction, a pair of primers is need, one positive-strand and one negative-strand situated respectively at the both end. The region defined by this pair of primers is the size of the PCR product. The oligonucleotide used in the PCR reaction for expanding the desired nucleic acid sequence can be double-strand or single-strand. In the present invention, the primer can be synthesized (e.g. chemically synthesized), for example, by the habitually know chemical method of phosphate-triester or phosphite amide. Primers can also be produced in vitro by the nucleotide sequence expansion method. If the expanded oligonucleotide is double-strand, then it can be converted to a single-strand molecule protect the single-strand oligonucleotide from the active action of the exonuclease. Furthermore, the primers mentioned in this invention are derived from the recombination plasmid of the insert which has the corresponding nucleotide sequence; the later can be split and retrieved from the selected plasmid by using the proper nucleotide if needed, splitting method such as classification of molecular weight can be used.

According to the method of the present invention, a conserved sequence within 3'-untranslated nucleotide sequence (SEQ ID NO:1) equivalent to LPC is chosen to design a pair of CSFV specific primers for performing RT-PCR reaction to distinguish the field isolates of CSFV from the lapinized vaccine virus by comparing to the size of the segment on the electrophoresis film. As for those who are familiar with the prior art, the letter "R" in the nucleotide sequence of the primers mentioned in this text refers to the base A or G unless otherwise specified.

In the preferred embodiment of this invention, the specific primers of CP-3F (5'-ACCCTRTTGTARATAACACTA-3'), identified as SEQ ID NO:3, and CP-3R (5'-GTTAAAAAT-GAGTGTAGTGTGGTA-3'), identified as SEQ ID NO:4 designed from the conserved region are used to amplify the different genotypes of CSFV to perform RT-PCR amplification. The length of the RT-PCR product after amplification is 127 bp for field isolates of CSFV and 140 bp for LPC vaccine virus. Therefore, the field isolates of CSFV and the lapinized vaccine strain can directly be distinguished from the result of the electrophoresis analysis without performing the DNA sequencing. In another embodiment of this invention, for increasing the sensitivity of the test, a nest-PCR (n-PCR) CSFV testing method is designed as to first amplify the CSFV specific primers CP-5 (5'-GTAGCAAGACTGGAAATAG-GTA-3'), identified as SEQ ID NO:5, and CP-6 (5'-AAAGT-GCTGTTAAAAATGAGTG-3'), identified as SEQ ID NO:6, of different genotypes of CSFV for the first RT-PCR amplification, then the product of the first amplification (the length for field isolates of CSFV is 367 bp and LPC vaccine virus is 380 bp respectively); is taken as template to perform nest-PCR using CP-3F and CP-3R as primers. The length of the obtained PCR product is 127 bp for field isolates of CSFV and 140 bp for LPC vaccine virus. In one other embodiment, using CP-3F (5'-ACCCTRTTGTARATAACACTA-3'), identified as SEQ ID NO:3, and CP-9R (5'-GTACCAGTTCT-TRCTCATTCAATA-3'), identified as SEQ ID NO:7, as primers, the amplified product of nest-PCR is 89 bp for field isolates of CSFV and 102 bp for LPC vaccine virus; only that the PCR product using this pair of primers is less. The nest-PCR is of high sensitivity and can conduct a high-quality testing result to chronic classical swine fever with low virus titer or CSFV carrier pigs with normal appearance.

According to the method of this invention, a RT-PCR diagnostic kit for determining the existence of field isolates of CSFV or lapinized vaccine virus in the samples is developed, either by a one-step RT-PCR diagnostic method to detect the CSFV or/and by furthermore using the nest-PCR to distinguish the filed isolates of CSFV from lapinized CSF vaccine viruses.

The term "samples" in this text refers to any biological material directly collected from a seemingly infected swine or enriched ones. The biological material can be any expectoration, bronchus alveolar lavage, blood, skin tissue, lymphatic tissue, living tissue specimens, semen, cultivated lymphocyte or blood, specimen of excrement and urine. The biological material can also be culture object or solution of artificially infected cellules.

BRIEF DESCRIPTION OF THE DRAWINGS

FIG. 4 shows SEQ ID NO: 1. The sequence of LPC vaccine virus between primers CP5 and CP6 (length 380 bp).

FIG. 5 shows SEQ ID NO: 2. The sequence of Alfort187 strain of CSFV, between primers CP5 and CP6 (length 367 bp), sequence position on the Alfort187 (Accession No: X87939) is from 11,874 to 12,240.

DETAILED DESCRIPTION OF THE PREFERRED EMBODIMENTS

Although the present invention is to be explained in relation to its preferred embodiment as illustrated in the following examples, it is not meant to limit the scope of the invention. It is to be understood that many other possible modifications and variations can be made by those skilled in the art without departing from the spirit and scope of the invention claimed.

Example 1

A one-step RT-PCR for distinguishing the field isolates of CSFV from the lapinized CSF vaccine viruses.

(1) Design of the Primers

A pair of amplification primers is designed from the conserved sequence within 3'-untranslated region of CSFV. This primer is a CSFV specific primer, which can only amplify the CFS virus but not its two close relatives bovine viral diarrhea virus (BVDV) and border disease virus (BDV). This primer is also one of the universal primers, which can be used to amplify different genotypes of CSFV. The nucleotide sequence of this primer pair is as follows:

```
                                           (SEQ ID NO:3)
    CP-3F     (5'-ACCCTRTTGTARATAACACTA-3')

(SEQ ID NO:4)
    CP-3R     (5'-GTTAAAAATGAGTGTAGTGTGGTA-3')
```

(2) Virus Sources

The lymphatic tissues of internal organs of swine such as tonsil, lymph node and spleen are ground with a mortar, then MEM medium (minimal essential medium) is added to form a 10% (w/v) suspension. After 20 minutes of 3000×g centrifugation, the top layer is retrieved for performing the RT-PCR. Alternatively, the cell culture of PK-15 cell infected by CSFV can also be used to perform RT-PCR.

(3) Extraction of Nucleic Acid

Add 100 μL of the top layer of the above-mentioned swine tissue emulsion or the cell culture solution into 1 mL of TRIzol total RNA extraction reagent. Mix with a vibrator for 30 seconds, place under room temperature for 5 minutes, add in 200 μL of chloroform, after 15 seconds of mixing, leave it still for another 3 minutes, centrifuge at 4° C. and 12,000 rpm for 15 minutes, retrieve the top layer and put in a clean centrifugal tube, add an equivalent volume of isopropyl alcohol and shake it up and down to get a uniform mixture, leave it still under room temperature for 10 minutes, centrifuge at 4° C. and 12,000 rpm for 15 minutes, remove all the solution, leave it still under room temperature for 10 to 15 minutes, and add 100 μL RNase-free secondary distilled water to dissolve it for further use.

(4) Single-Tube RT-PCR

Figure 1:
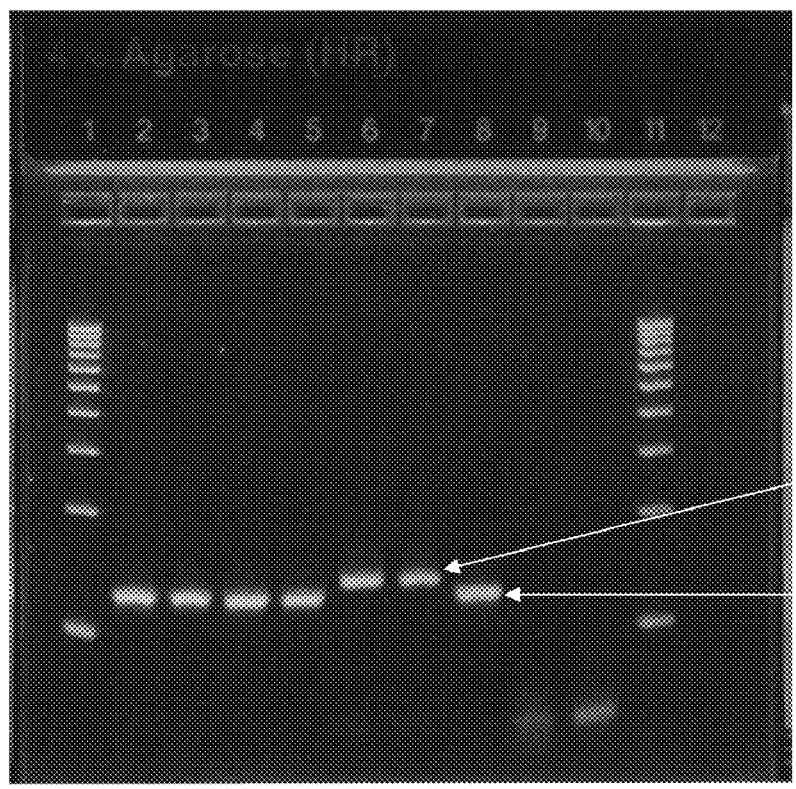
FIG. 1 is the electrophoretogram showing the result of electrophoresis (with a 4% agarose gel) of the product of the one-step RT-PCR (using CP-3F and CP-3R as primers) of the field isolates of CSFV and lapinized CSF vaccine virus from different sources. Wherein Lane 1 is 100 bp Ladder marker, Lane 2 is the 92-TC1 strain of field isolate of CSFV (2.1a subgroup), Lane 3 is the 90-YL5 strain of field isolate of CSFV (2.1b subgroup), Lane 4 is the 84-KS1 strain of field isolate of CSFV (2.2 subgroup), Lane 5 is the S-59 strain of field isolate of CSFV (3.4 subgroup), Lane 6 is the 93-TD1 strain, which is a field isolate of LPC vaccine virus (1.1 subgroup), Lane 7 is the positive control of the LPC vaccine virus, Lane 8 is ALD strain as the positive control, which is a virulent CSFV, Lane 9 is the BVDV, Lane 10 is the negative control and Lane 11 is the 100 bp Ladder marker.

This experiment is a single-tube one-step reaction, i.e. the reverse transcription (RT) and the polymerase chain reaction (PCR) proceed in a single reaction tube. All the necessary reagents are added into the same reaction tube at the same time. The characteristic of this experiment is the easy operation, which saves time and labor. Take 5 μL of the prepared nucleic acid sample, add the pair of CSFV specific primers CP-3F and CP-3R (20 pm), 5 μL of 10× Super Thermal buffer, 2 Unite (U) of RNase inhibitor (Promega), 2 U of AMV reverse transcriptase (Promega), 1 U of polymerase and 8 μL (1.25 mM) of dNTP, furthermore, add DEPC treated secondary distilled water to bring the final reaction volume to 50 μL. In the thermal circulation reaction machine (ABI 9600), the reverse transcription reaction is carried out at 42° C. for 40 minutes, then the PCR reaction is carried out at 95° C. for 1 minute, followed by 35 consecutive rounds of 94° C. for 40 seconds, 55° C. for 40 seconds, and 72° C. for 40 seconds, then the tube is kept at 72° C. for 7 minutes and stored at 4° C. The product of the RT-PCR reaction is analyzed by electrophoresis with 4% of agarose gel. As shown in the electrophoretogram of FIG. 1, the length of the products of one-step RT-PCR is 127 bp for field isolates of CSFV and 140 bp for LPC vaccine virus, respectively.

Example 2

For increasing the sensitivity of the test, another method using nest-PCR is designed for distinguishing the field isolates of CSFV from the lapinized CSF vaccine virus in addition to the one-step RT-PCR to detect the CSFV. The method is as follows:

(1) Design of the Primers

A pair of amplification primers is designed from the outer side of the amplification region of the CP-3F and CP-3R primers. This pair of primers is CSFV specific primers, which only amplifies the CSFV but not the two close relatives, BVDV and BDV. This pair of primers is one of the universal primers designed from the conserved sequences of CSFV, i.e. it can be used for CSF virus of all genotypes. The nucleotide sequence of this pair of primers is as follows:

```
                                           (SEQ ID NO:5)
    CP-5     5'-GTAGCAAGACTGGAAATAGGTA-3'

(SEQ ID NO:6)
    CP-6     5'-AAAGTGCTGTTAAAAATGAGTG-3'
```

(2) Single-Tube RT-PCR

Figure 2:
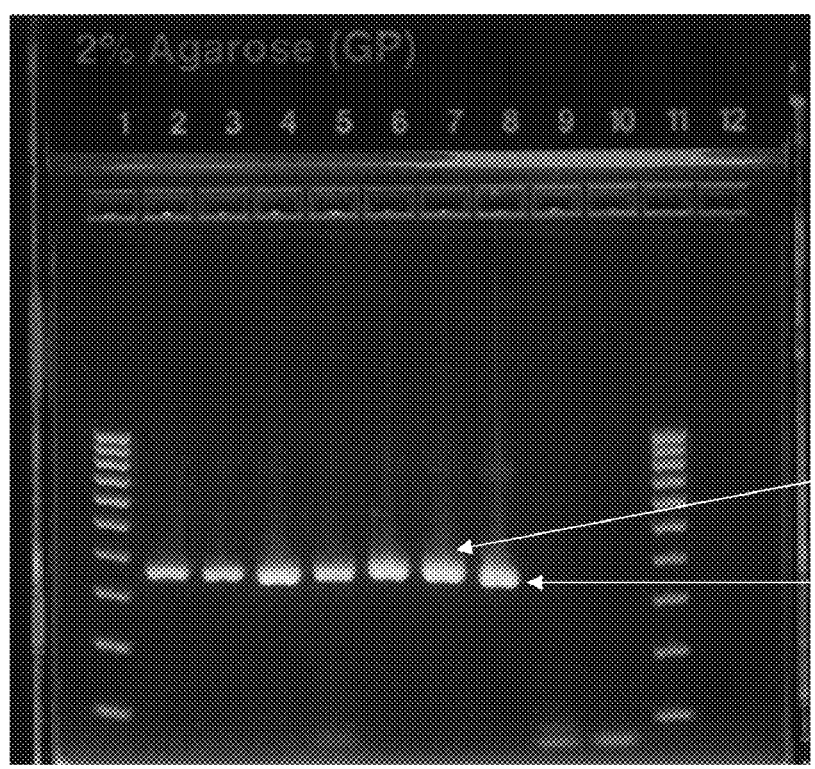
FIG. 2 is the electrophoretogram showing the result of electrophoresis (with a 2% agarose gel) of the product of the one-step RT-PCR (using CP-5 and CP-6 as primers) of the field isolate of CSFV and lapinized CSF vaccine virus from different sources. Wherein Lane 1 is the 100 bp Ladder marker, Lane 2 is the 92-TC1 strain of field isolate of CSFV (2.1a subgroup), Lane 3 is the 90-YL5 strain of field isolate of CSFV (2.1b subgroup), Lane 4 is the 84-KS1 strain of field isolate of CSFV (2.2 subgroup), Lane 5 is the S-59 strain of field isolate of CSFV (3.4 subgroup), Lane 6 is the 93-TD1 strain, which is a field isolate of LPC vaccine virus (1.1 subgroup), Lane 7 is the positive control of the LPC vaccine strain, Lane 8 is ALD strain as the positive control, which is a virulent CSFV, Lane 9 is the BVDV, Lane 10 is the negative control and Lane 11 is the 100 bp Ladder marker.

Take 5 μL of the prepared nucleic acid sample, add the pair of CSFV specific primers CP-5 and CP-6 (20 pm), 5 μL of 10× Super Thermal buffer, 2 U of RNase inhibitor (Promega), 2 U of AMV reverse transcriptase (Promega), 1 U of polymerase and 8 μL (1.25 mM) of dNTP, furthermore, add DEPC treated secondary distilled water to bring the final reaction volume to 50 μL. In the thermal circulation reaction machine (ABI 9600), the RT reaction is carried out at 42° C. for 40 minutes, then the PCR reaction is carried out at 94° C. for 1 minute, followed by 35 consecutive rounds of 94° C. for 40 seconds, 55° C. for 40 seconds, and 72° C. for 40 seconds, then the tube is kept at 72° C. for 7 minutes and stored at 4° C. The product of the RT-PCR reaction is analyzed by electrophoresis with 2% of agarose gel. As shown in the electrophoretogram of FIG. 2, the length of one-step RT-PCR products is 367 bp for field isolates of CSFV and 380 bp for LPC vaccine virus, respectively.

Figure 3:
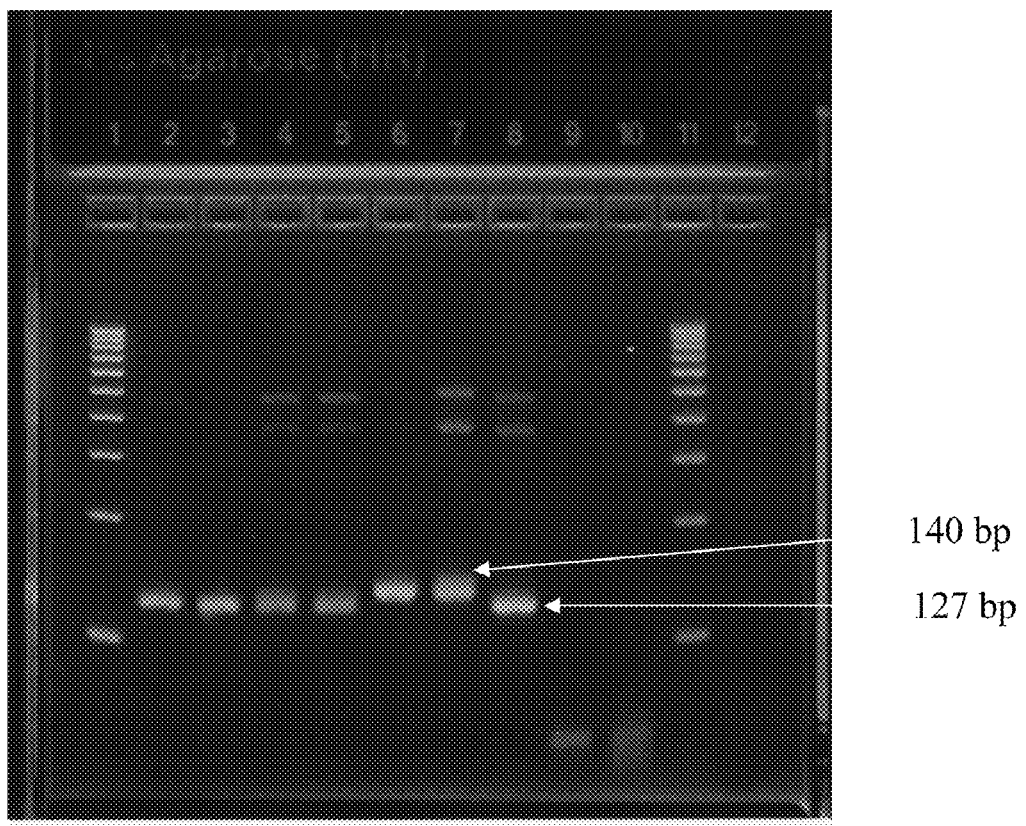
FIG. 3 is the electrophoretogram showing the result of electrophoresis (with a 4% agarose gel) of the product of the nest-PCR (using CP-3F and CP-3R as primers) of the field isolate of CSFV and lapinized CSF vaccine virus from different sources. Wherein Lane 1 is the 100 bp Ladder marker, Lane 2 is the 92-TC1 strain of field isolate of CSFV (2.1a subgroup), Lane 3 is the 90-YL5 strain of field isolate of CSFV (2.1b subgroup), Lane 4 is the 84-KS1 strain of field isolate of CSFV (2.2 subgroup), Lane 5 is the S-59 strain of field isolate of CSFV (3.4 subgroup), Lane 6 is the 93-TD1 strain, which is a field isolate of LPC vaccine virus (1.1 subgroup), Lane 7 is the positive control of the LPC vaccine virus, Lane 8 is ALD strain as the positive control, which is a virulent CSFV, Lane 9 is the BVDV, Lane 10 is the negative control and Lane 11 is the 100 bp Ladder marker.

(3) Nest-PCR for Distinguishing the Field Isolates of CSFV From the Lapinized CSF Vaccine Virus 2 μL of the first PCR product is taken as template. Add the above-mentioned primers CP-3F and CP-3R (20 pm), 5 μL of 10× Super Thermal buffer, 1 U of DNA polymerase and 8 μL (1.25 mM) of dNTP, furthermore, add DEPC treated secondary distilled water to bring the final reaction volume to 50 μL. In the thermal circulation reaction machine (ABI 9600), the polymerase chain reaction is carried out directly under 35 consecutive rounds of 94° C. for 35 seconds, 55° C. for 30 seconds, and 72° for 30 seconds, then the tube is kept at 72° C. for 7 minutes and stored at 4° C. The RT-PCR reaction solution is then subjected to electrophoresis for 40 minutes with agarophyte gel solution. As shown in the electrophoretogram of FIG. 3, the length of the products of nest-PCR is 127 bp for field isolates of CSFV and 140 bp for LPC vaccine virus, respectively.

As can been seen from the experimental results above, this invention provides a rapid and easy method to distinguish and identify the field isolates of CSFV and lapinized CSF vaccine virus based on the electrophoresis result without further performing nucleotide-sequencing or enzymetic digestion.

While the present invention has been described above in terms of specific embodiments, it is to be understood that the invention is not limited to these disclosed embodiments. Many modifications and other embodiments of the invention will come to mind of those skilled in the art to which this invention pertains; they are intended to be and are covered by both this disclosure and the appended claims. It is intended that the scope of the invention be determined by proper interpretation and construction of the appended claims and their legal equivalents, as understood by those skilled in the art relying upon the disclosure in this specification and the attached drawings.

What is claimed is:

1. A method for distinguishing wild-type classical swine fever virus (CSFV) from lapinized CSF vaccine viruses in an infected subject comprising:
   a) extracting total RNA from said subject;
   b) providing a pair of primers for polymerase chain reaction (PCR) comprising a forward degenerate primer selected from SEQ ID NO:3 and a reverse degenerate primer selected from SEQ ID NO:4, SEQ ID NO:6 or SEQ ID NO:7;
   c) using said RNA as template and performing a reverse transcription-PCR (RT-PCR) with said pair of primers provided in step b); and
   d) determining the existence of said wild-type CSFV or said lapinized CSF vaccine viruses according to RT-PCR products which said vaccine viruses is at least 12 nucleotides longer than said wild-type CSFV by electrophoresis.

2. The method as claimed in claim 1, further comprising: providing a pair of CSFV specific primers designed from the upstream and downstream sequence of an at least 12 nucleotides insertion in the 3'-untranslated region of the lapinized CSF vaccine viruses as compared to the wild-type CSFV; and using the pair of CSFV specific primers from step b) with the product of the RT-PCR to perform a nest-PCR.

3. The method as claimed in claim 1, further comprising a comparison of a gel electrophoresis analysis result for a RT-PCR product of a sample and said referenced lapinized CSF vaccine viruses.

4. The method as claimed in claim 2, wherein said pair of CSFV specific primers for RT-PCR comprises the following nucleotide sequences: SEQ ID NO:5 and SEQ ID NO:6,
   and said pair of CSFV specific primers for nest-PCR comprises: SEQ ID NO:3 and SEQ ID NO:4.

5. The method as claimed in claim 2, wherein said pair of CSFV specific primers for said RT-PCR comprises: SEQ ID NO:5 and SEQ ID NO:6,
   and said pair of CSFV specific primers for nest-PCR comprises: SEQ ID NO:3 and SEQ ID NO:7.

* * * * *

```
                        SEQUENCE LISTING

<160> NUMBER OF SEQ ID NOS: 9

<210> SEQ ID NO 1
<211> LENGTH: 380
<212> TYPE: DNA
<213> ORGANISM: Artificial Sequence
<220> FEATURE:
<223> OTHER INFORMATION: LPC Vaccine
<220> FEATURE:
<221> NAME/KEY: misc_difference
<222> LOCATION: (1)..(380)

<400> SEQUENCE: 1
gtagcaagac tggaaatagg tacatgcccg gagaaggcca caccctgcaa ggaagacatt        60
atgaagaatt ggtgttggca aggaaacaga tcaacaactt tcaagggaca gacaggtaca       120
atctaggccc aatagtcaac atggtgttga ggaggctgag agtcttgatg atgaccttga       180
tagggagagg ggtatgagcg cgggtaatct gggatctgaa cccgccagta ggaccctatt       240
gtagataaca ctaattttct tttttctttt tttatttatt tagattttat tatttattta       300
tttatttatt tattgaatga gtaagaattg gtacaaacta cctcaagtta ccacactaca       360 ctcatttta acagcacttt                                                    380

<210> SEQ ID NO 2
<211> LENGTH: 367
<212> TYPE: DNA
<213> ORGANISM: Classic Swine Fever Virus
<220> FEATURE:
<221> NAME/KEY: misc_difference
<222> LOCATION: (1)..(367)

<400> SEQUENCE: 2
gtagcaagac tggaaacagg tacataccctg gagagggcca caccctgcaa gggagacatt       60
atgaagaact ggtgttggca agaaaacaga tcaataactt tcaagggaca gacaggtaca      120
```

-continued

```
atctaggccc aatagtcaac atggtgttaa ggaggctgag agtcatgatg atgaccctga      180
tagggagagg ggtatgaacg cgggcaaccc gggatctgga cccgccagta ggaccctatt      240
gtagataaca ctaattttt atttatttag atattattat ttatttattt atttatttat      300
tgaatgagta agaactggta caaactacct caagttacca cactacactc attttaaca      360 gcacttt                                                                367
```

```
<210> SEQ ID NO 3
<211> LENGTH: 21
<212> TYPE: DNA
<213> ORGANISM: Artificial Sequence
<220> FEATURE:
<223> OTHER INFORMATION: CP-3F primer
<220> FEATURE:
<221> NAME/KEY: primer_bind
<222> LOCATION: (1)..(21)

<400> SEQUENCE: 3
accctrttgt arataacact a                                                21
```

```
<210> SEQ ID NO 4
<211> LENGTH: 24
<212> TYPE: DNA
<213> ORGANISM: Artificial Sequence
<220> FEATURE:
<223> OTHER INFORMATION: CP-3R primer
<220> FEATURE:
<221> NAME/KEY: primer_bind
<222> LOCATION: (1)..(24)

<400> SEQUENCE: 4
gttaaaaatg agtgtagtgt ggta                                             24
```

```
<210> SEQ ID NO 5
<211> LENGTH: 22
<212> TYPE: DNA
<213> ORGANISM: Artificial Sequence
<220> FEATURE:
<223> OTHER INFORMATION: CP-5 primer
<220> FEATURE:
<221> NAME/KEY: primer_bind
<222> LOCATION: (1)..(22)

<400> SEQUENCE: 5
gtagcaagac tggaaatagg ta                                               22
```

```
<210> SEQ ID NO 6
<211> LENGTH: 22
<212> TYPE: DNA
<213> ORGANISM: Artificial Sequence
<220> FEATURE:
<223> OTHER INFORMATION: CP-6 primer
<220> FEATURE:
<221> NAME/KEY: primer_bind
<222> LOCATION: (1)..(22)

<400> SEQUENCE: 6
aaagtgctgt taaaaatgag tg                                               22
```

```
<210> SEQ ID NO 7
<211> LENGTH: 24
<212> TYPE: DNA
<213> ORGANISM: Artificial Sequence
<220> FEATURE:
<223> OTHER INFORMATION: CP-9R primer
<220> FEATURE:
```

```
<221> NAME/KEY: primer_bind
<222> LOCATION: (1)..(24)

<400> SEQUENCE: 7
gtaccagttc ttrctcattc aata                                              24

<210> SEQ ID NO 8
<211> LENGTH: 12
<212> TYPE: DNA
<213> ORGANISM: Artificial Sequence
<220> FEATURE:
<223> OTHER INFORMATION: 3'-untranslated region of HCLV genomic cDNA
<220> FEATURE:
<221> NAME/KEY: 3'UTR
<222> LOCATION: (1)..(12)

<400> SEQUENCE: 8
cttttttctt tt                                                           12

<210> SEQ ID NO 9
<211> LENGTH: 13
<212> TYPE: DNA
<213> ORGANISM: Artificial Sequence
<220> FEATURE:
<223> OTHER INFORMATION: 3'-untranslated region of LPC vaccine strain
<220> FEATURE:
<221> NAME/KEY: 3'UTR
<222> LOCATION: (1)..(13)

<400> SEQUENCE: 9
tttycttttt ttt                                                          13
```